United States Patent
Kroll

(10) Patent No.: US 6,327,498 B1
(45) Date of Patent: Dec. 4, 2001

(54) IMPLANTABLE STIMULATION LEAD FOR USE WITH AN ICD DEVICE HAVING AUTOMATIC CAPTURE PACING FEATURES

(75) Inventor: Mark W. Kroll, Orono, MN (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/168,207

(22) Filed: Oct. 7, 1998

(51) Int. Cl.⁷ .................................. A61N 1/39; A61N 1/05
(52) U.S. Cl. .......................... 607/4; 607/116; 607/122; 607/5; 600/509
(58) Field of Search ................................ 607/122, 123, 607/116, 4, 5, 28; 600/509

(56) References Cited

U.S. PATENT DOCUMENTS

| | | | |
|---|---|---|---|
| 3,977,411 | 8/1976 | Hughes, Jr. et al. | 128/419 P |
| 4,355,646 | 10/1982 | Kallok et al. | 128/786 |
| 4,712,557 | 12/1987 | Harris | 128/419 P |
| 5,314,430 | 5/1994 | Bardy | 607/5 |
| 5,324,310 | 6/1994 | Greeninger et al. | 607/28 |
| 5,334,045 | 8/1994 | Cappa et al. | 439/506 |
| 5,336,253 | 8/1994 | Gordon et al. | 607/122 |
| 5,342,414 | 8/1994 | Mehra | 607/127 |
| 5,405,375 | 4/1995 | Ayers et al. | 607/122 |
| 5,411,529 | 5/1995 | Hudrlik | 607/6 |
| 5,456,706 * | 10/1995 | Pless et al. | 607/122 |
| 5,476,502 | 12/1995 | Rubin | 607/127 |
| 5,531,782 | 7/1996 | Kroll et al. | 607/122 |
| 5,534,022 * | 7/1996 | Hoffmann et al. | 607/122 |
| 5,545,183 | 8/1996 | Altman | 607/5 |
| 5,557,210 | 9/1996 | Cappa et al. | 324/539 |
| 5,591,218 | 1/1997 | Jacobson | 607/63 |
| 5,702,427 | 12/1997 | Ecker et al. | 607/28 |

* cited by examiner

*Primary Examiner*—Kennedy Schaetzle

(57) ABSTRACT

An implantable ICD stimulation lead system for implantation in a human heart having electrodes adapted to be energized selectively to achieve pacing in one instance, true bipolar sensing in another instance suitable for autocapture detection, and defibrillation in close proximity to the ventricular apex in still another instance. The stimulation system comprises an elongated insulated lead body having a distal tip electrode and two multipurpose electrodes which are selectable for defibrillation or bipolar sensing purposes. True bipolar pacing is achieved between a primary shocking electrode space approximately 1.7–3.0 cm from the tip electrode, and a secondary shocking electrode may be selectively used in parallel with the primary shocking electrode to achieve lower thresholds due to its closer proximity to the ventricular apex.

12 Claims, 2 Drawing Sheets

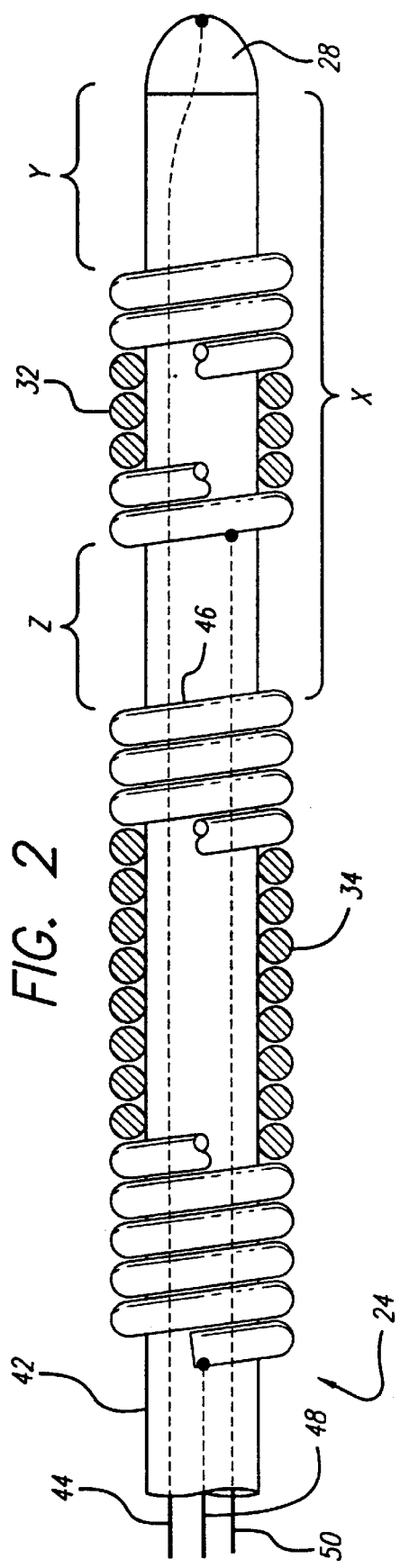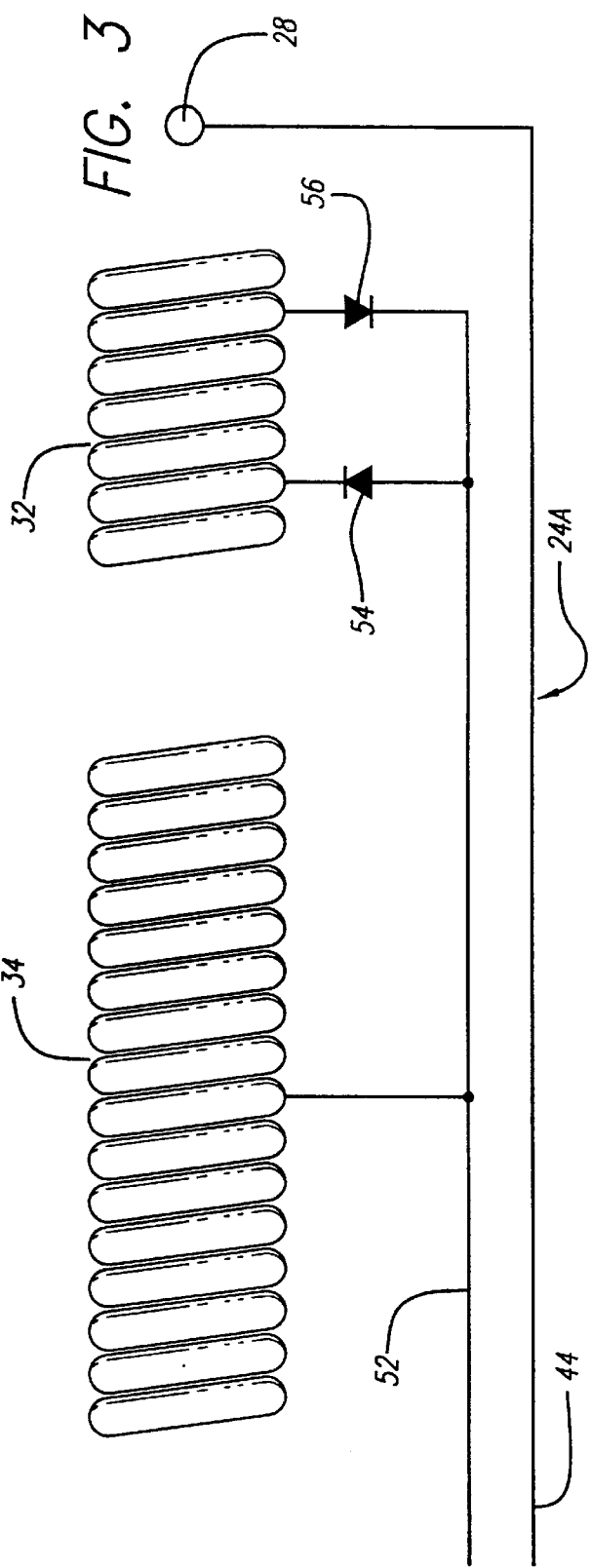

IMPLANTABLE STIMULATION LEAD FOR USE WITH AN ICD DEVICE HAVING AUTOMATIC CAPTURE PACING FEATURES

FIELD OF THE INVENTION

The present invention relates generally to implantable stimulation leads for use in the detection and control of cardiac bradyarrhythmias and tachyarrhythmias, and more particularly to a lead including an arrangement of cardioversion/defibrillation electrodes and pacing/sensing electrodes on a common lead body which optimize both defibrillation thresholds and sensing thresholds which in turn enable automatic capture algorithms to function properly.

BACKGROUND OF THE INVENTION

In recent years there has been a great deal of interest and progress in the integration of implantable medical devices such as defibrillators and pacemakers. For the purpose of this application, "defibrillation" is used in a broad sense, as including the application of relatively high energy and high voltage shocks to the heart to terminate tachyarrhythmias including fibrillation and malignant tachycardias. Similarly, "pacing" is used in a broad sense, as including the application of relatively low energy and low voltage pacing pulses to maintain an adequate heart rate or to break a tachycardia by stimulating the patient's heart.

It is well known that automatic capture algorithms ensure that capture is maintained even in the presence of changing physiologic conditions and drugs. In view of the direction of current implantable cardioverter/defibrillator (ICD) designs, it would be desirable to offer automatic capture pacing in a combination device having pacing and defibrillating functionality. It is also well known that automatic capture requires "true" bipolar sensing, that is, tip to ring sensing, or at least unipolar sensing from the bipolar ring electrode to the case electrode.

One traditional approach to combining pacing and true bipolar sensing electrodes in a defibrillation lead is to provide a ring electrode located between the pacing tip electrode and the defibrillation electrode where the ring electrode is dedicated exclusively to sensing the heart's electrical activities. However, the optimal spacing for autocapture sensing has been found to be in the range of 1.7–3.0 (and preferable about 2.5 cm) from the tip electrode to the ring electrode. In an ICD lead, it is desirable to have the shocking coil as close as possible to the RV apex to lower defibrillation thresholds. ICD leads strive to have the shocking coil spaced down about 1.2 cm from the end. The space required for this ring electrode forces the defibrillation electrode to be set back from the RV apex, and, because of the size limitations of the right ventricle, decreases the length available for the defibrillation electrode. This would severely increase fibrillation thresholds.

However, in the context of endocardial ventricular leads, it would be desirable to provide an electrode, or electrode pair, for sensing adjacent the ventricular apex, while still providing an electrode which also is located as close to the apex as possible. Exemplary attempts to accomplish such an objective are described in U.S. Pat. No. 5,336,253, to Gordon et al. and U.S. Pat. No. 5,342,414 to Mehra.

The Gordon et al. patent describes a combined pacing and cardioversion lead system with internal electrical switching components for unipolar or bipolar sensing of electrograms, pacing at normal pacing voltages and cardioversion or defibrillation. In the bipolar embodiments, a ring electrode is coupled through the switching circuitry to a large surface area cardioversion electrode. In these embodiments, pacing and sensing are accomplished though a pair of conductors extending through the lead body to the tip and ring electrodes. When cardioversion shocks are delivered to the ring electrode, cardioversion energy is also directed to the cardioversion electrode through the operation of the switching circuitry in response to the magnitude of the applied cardioversion pulse. However, for optimal automatic capture sensing the ring electrode should be spaced approximately 2.5 cm from the tip, as noted above. This would place the composite defibrillation electrode, as taught by Gordon, 2.5 cm from the tip, which would increase defibrillation thresholds.

The transvenous defibrillation lead described in the Mehra patent is directed towards optimizing the size, spacing and location of the electrodes, and more specifically towards providing a bipolar sensing pair of electrodes having adequate interelectrode spacing to insure appropriate sensing of cardiac depolarization, while still allowing the placement of the electrode as close to the distal end of the lead body as possible. The lead includes a helical electrode, extending distally from the lead body, for use as the active electrode in cardiac pacing and for use in sensing cardiac depolarizations. A ring electrode is located at or adjacent to the distal end of the lead body and provides the second electrode for use in sensing depolarizations. The helical electrode is insulated from the point it exits the lead body until a point adjacent to is distal end. The defibrillation electrode is mounted with its distal end closely adjacent to the distal end of the lead body, such that its distal end point is within one centimeter of the distal end of the lead body. While the Mehra reference seems to address the needs of placing the defibrillation coil closer to the apex, it neglects the need to place the pacing ring electrode about 2.5 cm away from the pacing tip electrode.

U.S. Pat. No. 4,355,646 to Kallok et al. teaches the use of two rigid equal width electrodes placed in the right ventricle. However, the efficacy of this construction is questioned because it is optimized for sensing contractions via impedance changes. It could not reliably electrically sense postshock since it requires full force shocking through the most distally located electrode. To the knowledge of the applicant, this concept has never been practiced commercially.

The leads described in the foregoing Gordon et al., Mehra, and Kallok et al. patents do not provide for "integrated electrogram bipolar sensing", wherein sensing is carried out between the defibrillation shocking coil electrode and the tip electrode. One feature that distinguishes integrated bipolar sensing and true bipolar sensing (i.e., pacing ring-to-tip sensing) is that integrated bipolar sensing lacks a ring electrode dedicated solely to bipolar sensing in conjunction with the pacing tip.

There are two potential problems with integrated bipolar electrodes. First, because the reference electrode must be large for efficient delivery of defibrillation or cardioversion energy, it may reduce the resolution of the sensed signal due to spatial averaging of the different potentials within the heart. Secondly, this electrode serves also as a defibrillation electrode and is likely to have substantial residual charge at its interface after a defibrillation therapy pulse. The residual charge or polarization of the electrodes results in less accurate sensing immediately after therapy. The true bipolar sense lead should not be subject to these potential problems. The size of the true bipolar reference electrode is not governed by the need for efficient energy delivery during therapy and can be optimized for sensing.

Additionally, because a negligible current flows across the electrode tissue interface, there is no build-up of charge or polarization at the interface, enabling the accurate measurement of endocardial signals immediately following therapy. However, a drawback with true bipolar sensing exists because the reference sense electrode in a true bipolar lead is located adjacent to the pacing electrode, and thus the defibrillation shocking coil electrode is generally positioned farther away from the apex of the heart, thus disadvantageously reducing the delivered therapeutic energy.

More recently, the invention disclosed in U.S. Pat. No. 5,545,183 to Altman is directed towards providing a method and apparatus for using a defibrillation lead to defibrillate and sense in close proximity to the heart ventricular apex. In particular, the invention is directed towards providing a new method which permits the optimal delivery of defibrillation and cardioversion energies, and the minimization of poor sensing due to polarization effect, by the selective use of the ring in parallel with the defibrillation coil to assist with difficult defibrillations. This has the same disadvantages as does the Gordon reference. That is, in order for the bipolar ring electrode to function properly for automatic capture, it must be placed about 2.5 cm away from the tip, which would put the defibrillation coil electrode even further away under normal operating conditions, and switchably to 2.5 cm only when the first defibrillation shock has failed.

It was with knowledge of the foregoing state of the technology that the present invention has been conceived and is now reduced to practice.

SUMMARY OF THE INVENTION

The present invention relates generally to an ICD lead system for implantation in a human heart having an electrode configuration compatible with current automatic capture pacing systems.

The basic concept of the invention concerns a lead having a two- or three-conductor construction with the conductors extending respectively to a primary shocking coil electrode, a secondary shocking coil electrode, and a distal tip electrode. The primary shocking coil is set back a distance of in the range of 1.7–3.0 cm from the distal tip electrode, wherein true bipolar sensing occurs between the distal end of the primary shocking coil and the distal tip electrode.

Interposed between the distal tip electrode and the primary shocking coil is the secondary shocking coil. The secondary shocking coil is set back a distance of about 1.2 cm from the distal tip electrode. During delivery of a shock, the ICD circuitry connects the primary shocking coil and the secondary shocking coil in a parallel so that the composite shocking coil can deliver the defibrillation current closer to the left ventricular apex.

More specifically, in one embodiment, the implantable ICD lead system comprises an elongated insulated lead body extending between a proximal end connected to a pulse generator and a distal end terminating at a distal tip electrode. A first conductor is contained within the lead body and electrically connects the pulse generator and the distal tip electrode. A primary shocking coil electrode on the lead body is spaced from the distal tip electrode. A second conductor is mounted on the lead body and extends between and electrically connects the pulse generator and the primary shocking coil electrode. A secondary shocking coil electrode contained within the lead body is spaced between, and electrically insulated from, the distal tip electrode and the primary shocking coil electrode. A third conductor electrically connects the pulse generator and the secondary shocking coil electrode.

The ICD device can then select the appropriate combination of electrodes to achieve pacing in one instance (i.e., between the secondary shocking coil electrode and the distal tip electrode), sensing in another instance (i.e., between the primary shocking coil electrode and the distal tip electrode), and defibrillation in still another instance (i.e., a composite of the primary and secondary coils coupled to the distal tip electrode). The distance between the primary shocking coil electrode and the distal tip electrode is preferably more than about 1.7 cm and no greater than about 3.0 cm. This allows for optimal sensing of automatic capture depolarization signals.

Depending on the circuitry and the ICD, the system allows great flexibility in the form of programmable polarity for the pathways for pacing and for sensing of ventricular fibrillation (VF). For example, pacing could be performed from tip to secondary shocking coil or from tip to primary shocking coil. Likewise, the sensing of VF could be performed from tip to secondary shocking coil or tip to primary shocking coil as well.

The invention also encompasses another implementation. In this instance, there are only two conductors and the lead could be used without any modification to an ICD. The secondary shocking coil is connected to the primary shocking coil and its conductor through a pair of diodes connected in antiparallel. During the delivery of a 750 V fibrillation shock, for example, the 0.7 V drop of these diodes has no impact as they lose about 0.1% of the shock voltage. However, during automatic capture sensing, the less than one volt drop of those diodes is still significantly greater than the millivolt signal found from the cardiac depolarization. Thus the cardiac depolarization signal will not flow through the secondary shocking coil connection; it will flow through the tip of the primary shocking coil. This allows the achievement of the optimal spacing of the tip and the primary shocking coil without harming the delivery of efficient delivery current into the apex.

A primary feature, then, of the present invention is to provide autocapture pacing in an implantable cardioverter defibrillator (ICD) system.

Another feature of the present invention is the provision of a defibrillation lead with the distal end of the primary shocking coil being more than 1.7–3.0 cm back from the tip of the lead so that autocapture sensing can occur using true bipolar sensing.

Another feature of the present invention is the provision of a defibrillation lead with the distal end of the secondary shocking coil being more than 1.2 cm back from the tip of the lead so that defibrillation thresholds are reduced.

Still another feature of the present invention is the provision of such an ICD lead system in which the lead has three electrodes and shock current is delivered to two of them while automatic capture sensing is done from a different pair.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 2 is a diagrammatic elevation view, certain parts being cut away and shown in section, of one embodiment of the invention; and FIG. 3 is a diagrammatic view of another embodiment of the invention.

DETAILED DESCRIPTION OF THE PREFERRED EMBODIMENTS

Figure 1:
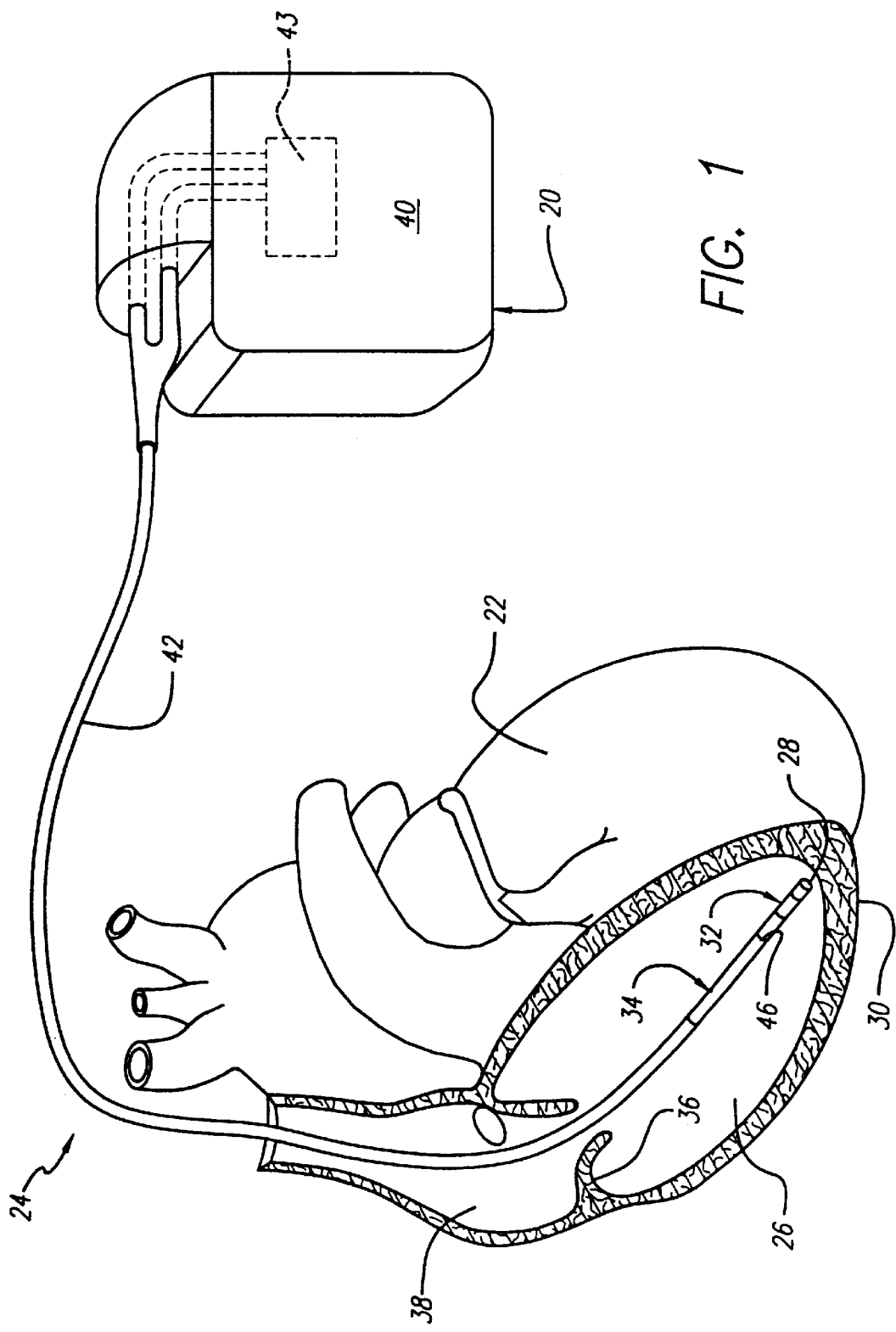
FIG. 1 is a diagrammatic, perspective, view, certain parts being cut away and in section for clarity, of an ICD lead system embodying the invention in operation.

Turn now to the drawings and, initially, to FIG. 1 which generally illustrates a cardiac stimulator 20 in the form of a ventricular pacemaker/cardioverter/defibrillator implanted, in a typical manner, subcutaneously between the skin and the ribs of the patient and in the left pectoral region of his heart 22. More specifically, an implantable ICD lead system 24 taught by the invention is passed through a vein into the right ventricle 26 of the heart 22. The distal end of the lead system 24 has a tip electrode 28 contacting the interior of the ventricle, preferably at its apex 30.

An elongated primary shocking coil electrode 34 is spaced a distance, X, of about 1.7–3.0 cm from the tip electrode 28, and preferable about 2.5 cm. The primary shocking coil extends in a direction towards the region of the tricuspid valve 36 between the right atrium 38 and the right ventricle 26 and typically has a length of about 2–6 cm.

A secondary shocking coil electrode 32 is located distal to the primary shocking coil electrode 34 and spaced a distance, Y, of about 1.2 cm from the tip electrode 28.

Each of these electrodes is connected, via the lead 24, to the circuitry contained in the cardiac stimulator 20. The metallic enclosure or "can" of the cardiac stimulator also forms an electrode surface 40.

Although a variety of lead configurations can be used to pace the heart 22, to sense the intrinsic depolarizations of the heart, and to deliver defibrillation or cardioversion pulses, the present invention is disclosed in a configuration where ventricular pacing is delivered using the tip electrode 28 and the secondary shocking coil electrode 32; and sensing is accomplished using the tip electrode 28 and the primary shocking coil electrode 34. Defibrillation is accomplished using the primary shocking coil electrode 34 and can electrode 40.

The implantable ICD lead system 24 will now be described in greater detail with reference to FIG. 2. Automatic capture pacing, such as found in the AutoCapture™ Pacing System embodied in selected pulse generators manufactured by Pacesetter, Inc. pacing is the technique of reducing the pacing energy to the minimum required to capture the heart. (AutoCapture™ is a trademark of pacesetter, Inc.) This is accomplished by verifying capture by sensing the depolarizations of the heart and lowering pacing amplitude until capture is lost. This can extend pacemaker lifetimes from between five to 15 years. It comprises the elongated insulated lead body 42 extending between a proximal end connected to a pulse generator 43 diagrammatically depicted within the cardiac stimulator 20, and a distal end terminating at the distal tip electrode 28. A first conductor 44 suitably contained within the lead body 42 extends between the pulse generator 43 and the distal tip electrode and electrically connects those components. The primary shocking coil, or defibrillation, electrode 34 on the lead body 42 has a distal end 46 which is spaced from the distal tip electrode by a distance of at least about 1.7 cm but no greater than about 3.0 cm. A second conductor 48 is suitably contained within the lead body, extends between the pulse generator 43 and the primary shocking coil electrode 34 and electrically connects those components. Further in keeping with the invention, the secondary shocking coil electrode 32 on the lead body 42 is spaced between, and electrically insulated from, the distal tip electrode 28 and the primary shocking coil electrode 34. A third conductor 50 is contained within the lead body 42 and extends between the pulse generator 43 and the secondary shocking coil electrode 32 and electrically connects those components.

When the lead system 24 is used in the defibrillation mode, the secondary shocking coil electrode 32 effectively becomes an extension of the primary shocking coil electrode 34 while for autocapture sensing, it is effectively inert. The secondary shocking coil electrode 32 is preferably flexible for ease of insertion and so as to properly conform to the shape of the chamber of the heart as it beats and capable of bending without being damaged. To this end, the secondary shocking coil electrode may be a coil or may be of some other suitable shape or construction. The maximum length of the secondary shocking coil, L, can be determined by the equation:

$$L = X - Y - Z$$

wherein:

X is the value chosen for the primary shocking coil (between 1.7 and 3.0 cm);

Y is the value chosen for the separation of the secondary shocking coil 32 from the tip electrode (preferably about 1.2 cm); and Z is the amount of insulation desired between the primary and the secondary shocking coils (at least about 0.2 cm).

Taking the full range of X and the minimum allowed for Y and Z would suggest a range for the length of the secondary shocking coil electrode 32 to be about 0.3–1.6 cm, and optimally the maximum size within manufacturing constraints.

In operation, in one instance, the distal tip electrode 28 is selectively energized to achieve pacing; in another instance, the distal tip electrode signal is selectively amplified for sensing in another instance; and the primary shocking coil electrode 34 is energized to achieve defibrillation in still another instance. For autocapture sensing, it is preferable that there be sufficient spacing between the primary shocking coil electrode 34 and the tip electrode 28 in order to obtain a good strong R-wave. For this purpose, spacing is preferably in the range of about 1.7 to 3.0 cm, and preferably about 2.5 cm. In this regard, if the leads are too close (less than about 1.7 cm) it becomes difficult to distinguish between noise and a true signal. On the other hand, for defibrillation, it is preferable that the spacing between the primary shocking coil electrode 34 and the tip electrode 28 be a minimum, but to accommodate the autocapture sensing functions, the spacing between the primary shocking coil electrode 34 and the distal tip electrode 28 is no less than about 1.7 cm. The secondary shocking coil serves as an extension of the primary shocking coil for defibrillation but serves as an inert spacer for autocapture sensing.

Another embodiment of the invention will now be described with reference to FIG. 3, specifically, the implantable ICD lead system 24A. In this instance, there are only two conductors, namely, a first conductor 44 to the tip electrode 28 and a second conductor 52 to which the primary shocking coil electrode 34 and the secondary shocking coil electrode 32 are serially connected, the relationship among the electrodes 28, 32, and 34 being generally as described with respect to the FIG. 2 embodiment. In actual fact, the secondary shocking coil electrode 32 is electrically connected to the conductor 52 via a pair of diodes 54, 56 connected in antiparallel and spaced from and between the tip electrode and the primary shocking coil electrode.

As previously mentioned, during the delivery of a 750 V fibrillation shock, for example, the 0.7 V drop of these diodes has no impact as they lose about 0.1% of the shock voltage. However, during autocapture sensing, the less than one volt drop of those diodes is still significantly greater than the millivolt signal found from the cardiac depolarization. Thus, the cardiac depolarization signal will not flow through the secondary shocking coil connection; it will flow through the tip of the primary shocking coil. This allows the achievement of the optimal spacing of the tip electrode 28 and of the primary shocking coil electrode 34 without harming the delivery of efficient delivery current into the apex 30.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable ICD lead system adapted to be coupled to a programmable implantable stimulation device having automatic capture algorithms therein, comprising:

an elongated insulated lead body having a proximal end adapted to be coupled to the stimulation device and a distal end, the lead body having first, second and third conductors extending between the proximal end and the distal end;

a distal tip electrode coupled to the first conductor at the distal end of the lead body;

a primary shocking coil electrode coupled to the second conductor and spaced from the distal tip electrode, wherein the distance between the primary shocking coil and the distal tip electrode is more than about 1.7 cm and no greater than about 3.0 cm;

a secondary shocking coil electrode spaced between, and electrically insulated from, the distal tip electrode and the primary shocking coil electrode; and a reference electrode adapted to be coupled to one of the lead body or the implantable stimulation device;

wherein true bipolar sensing, suitable for use for automatic capture sensing, may be programmed by the stimulation device between the primary shocking coil electrode and the distal tip electrode;

wherein the stimulation device may be programmed to deliver shock therapy through the primary and secondary shocking coils to the reference electrode.

2. An implantable ICD lead system adapted to be coupled to a programmable implantable stimulation device, comprising:

first electrode means for providing pacing stimulation pulses to ventricular heart tissue;

second electrode means for providing shocking stimulation pulses and for sensing true bipolar signals;

third electrode means, spaced between the first electrode means and the second electrode means, for providing shocking stimulation pulses in parallel with the second electrode means; and lead means, having a distal end, a proximal end adapted to be coupled to the stimulation device, and at least two conductors, for electrically coupling the first, second and third electrode means located at the distal end to the stimulation device, wherein the first electrode means is a distal tip electrode;

the second electrode means is a primary shocking coil electrode extending between proximal and distal ends, whose distal end is greater than about 1.7 cm distant from the distal tip electrode, wherein the third electrode means includes a secondary shocking electrode on the lead body intermediate the distal tip electrode and the primary shocking coil electrode; and pacing and sensing of the heart being selectively achieved by electrical current flow, respectively, between the tip electrode and the secondary shocking electrode and between the tip electrode and the primary shocking coil electrode.

3. The implantable ICD lead system, as set forth in claim 2, wherein the at least two conductors comprises:

a first conductor contained within the lead body extending between the proximal end and electrically connected to the first electrode at the distal end;

a second conductor contained within the lead body extending between the proximal end and the primary shocking coil electrode at the distal end; and wherein the secondary shocking electrode is electrically connected to the second conductor at the distal end thereof via a pair of diodes connected in antiparallel.

4. The implantable ICD lead system, as set forth in claim 3, wherein:

the distal end of the primary shocking coil is spaced from the distal tip electrode by about 1.7–3.0 cm.

5. An implantable ICD stimulation system comprising:

pulse generating means for generating pacing and shocking stimulation pulses;

a reference electrode;

a lead body having at least two conductors contained within and extending between a proximal end and a distal end, the proximal end being adapted to connect to the pulse generator;

first electrode means, located at the distal end of the lead body, for delivering the pacing stimulation pulses;

second electrode means, located on the lead body spaced from the first electrode means and connected to the pulse generator, for providing the shocking stimulation pulses and for sensing true bipolar signals between the first electrode means and the second electrode means;

third electrode means, spaced between the first electrode means and the second electrode means, for providing shocking stimulation pulses in parallel with the second electrode means; and control means for selectively pacing and sensing of the heart between the first electrode means and the second electrode means, and for selectively providing shocking therapy between the reference electrode and the second and third electrode means.

6. The implantable ICD stimulation system, as set forth in claim 5, wherein:

the first electrode means is a distal tip electrode; and the second electrode means is a primary shocking coil electrode extending between proximal and distal ends, whose distal end is no greater than about 1.7 cm distant from the distal tip electrode.

7. The implantable ICD stimulation system, as set forth in claim 6, wherein:

the third electrode means includes a secondary shocking electrode on the lead body intermediate the distal tip electrode and the primary shocking coil electrode; and pacing and sensing of the heart being selectively achieved by electrical current flow, respectively, between the tip electrode and the secondary shocking electrode and between the tip electrode and the primary shocking coil electrode.

8. The implantable ICD stimulation system, as set forth in claim 7, wherein the at least two conductors comprises:

first, second, and third conductors contained within the lead body, each of the conductors extending between the proximal end and electrically connected, respectively, to the first, second, and third electrodes at the distal end.

9. The implantable ICD stimulation system, as set forth in claim 7, comprising:

a first conductor contained within the lead body extending between the proximal end and electrically connected to the first electrode at the distal end;

a second conductor contained within the lead body extending between the proximal end and electrically connected to the second electrode at the distal end;

wherein the third electrode is electrically connected to the second conductor at the distal end via a pair of diodes connected in antiparallel.

10. The implantable ICD stimulation system, as set forth in claim 5, wherein:

the third electrode is a secondary shocking coil extending longitudinally of the lead body a distance about 0.3 cm–1.6 cm.

11. The implantable ICD stimulation system, as set forth in claim 5, wherein:

the secondary shocking coil of the third electrode is of a flexible construction.

12. An implantable ICD system comprising:

an elongated, insulated lead body having a proximal end and a distal end, the lead body having plural conductors extending between the proximal end and the distal end;

a distal tip electrode coupled to one of the conductors;

a primary shocking coil electrode coupled to one of the conductors, wherein the primary shocking coil is spaced from the distal tip electrode a predetermined distance;

a secondary shocking coil electrode interposed between the distal tip electrode and the primary shocking coil electrode and connected to one of the conductors; and a controller that is operative to selectively sense between the tip electrode and the primary shocking coil, the controller further being operative to control the simultaneous delivery of shocking therapy to both the primary and secondary shocking coil.

* * * * *